US007288243B2

(12) United States Patent
Knight et al.

(10) Patent No.: US 7,288,243 B2
(45) Date of Patent: Oct. 30, 2007

(54) AEROSOL DRUG INHIBITION OF LUNG METASTASES

(75) Inventors: J. Vernon Knight, Houston, TX (US); J. Clifford Waldrep, The Woodlands, TX (US); Nadezhda Koshkina, Houston, TX (US)

(73) Assignee: Research Development Foundation, Carson City, NV (US)

( * ) Notice: Subject to any disclaimer, the term of this patent is extended or adjusted under 35 U.S.C. 154(b) by 619 days.

(21) Appl. No.: 10/439,773

(22) Filed: May 16, 2003

(65) Prior Publication Data

US 2003/0215494 A1 Nov. 20, 2003

Related U.S. Application Data

(60) Provisional application No. 60/381,767, filed on May 20, 2002, now abandoned.

(51) Int. Cl.
*A61K 47/00* (2006.01)
*A61K 47/30* (2006.01)

(52) U.S. Cl. ............... 424/1.13; 424/1.21; 424/450

(58) Field of Classification Search ............... None
See application file for complete search history.

(56) References Cited

U.S. PATENT DOCUMENTS 6,090,407 A * 7/2000 Knight et al. ............... 424/450
6,090,955 A 7/2000 Reszka et al. ............... 549/510

FOREIGN PATENT DOCUMENTS

WO WO 98/00111 * 1/1998

OTHER PUBLICATIONS

Waldrep et al (International Journal of Pharmaceutics, 1993, vol. 97, pp. 205-212.*
Ross et al (Clinical Cancer Research, 1997, vol. 3, pp. 57-62).*
The abstract of Ross et al (Proceed Amer Assoc Cancer Res, Mar. 1999, vol. 40, p. 187).*
The abstract of Koshkina et al (Proceed Amer Assoc Cancer Res, Mar. 2001, vol. 42, p. 374).*
Cabanes et al., "Comparative in vivo studies with paclitaxel and liposome-encapsulated paclitaxel," *Int. J. Oncol.*, 12:1035-1040, 1998.
Choy et al., "The current state of paclitaxel and radiation in the combined-modality therapy of non-small cell lung cancer," *Semin. Oncol.*, 28(Suppl 14):17-22, 2001.
Cresteil et al., "Taxol metabolism by human liver microsomes: identification of cytochrome P450 isozymes involved in its biotransformation," *Cancer Res.*, 54:386-392, 1994.
Fujitaka et al., "Induction of cytochrome P450 3A4 by docetaxel in peripheral mononuclear cells and its expression in lung cancer," *Cancer Chemother. Pharmacol.*, 48:42-46, 2001.
Germann, "Detection of recombinant P-glycoprotein in multidrug resistant cultured cells," *Mol. Biotechnol.*, 14:131-145, 2000.
Gilbert et al., "Characterization and administration of cyclosporine liposomes as a small-particle aerosol," *Transplantation*, 56:974-977, 1993.
Gilbert et al., "Cyclosporin a Liposome Aerosol: Lack of Acute Toxicity in Rats with a High Incidence of Underlying Pneumonitis," *Inhalation Taxicology*, 9:717-730, 1997.
Gilbert et al., "Tolerance of volunteers to cyclosporine A—dilauroylphosphatidylcholine liposome aerosol," *Am. J. Respir. Crit. Care Med.*, 156:1789-1793, 1997.
Gottesman et al., "Biochemistry of multidrug resistance mediated by the multidrug transporter," *Annu. Rev. Biochem.*, 62:385-427, 1993.
Knight et al., "Anti-cancer activity of 9-nitrocaptothecin liposome aerosol in mice," *Transactions of the American Clinical and Climatological Association*, 111:135-145, 2000.
Knight et al., "Anticancer effect of 9-nitrocamptothecin liposome aerosol an human cancer xenografts in nude mice," *Cancer Chemother. Pharmacol.*, 44:177-86, 1999.
Koshkina et al., "9-Nitrocamptothecin liposome aerosol treatment of melanoma and osteosarcoma lung metastases in mice," *Clinical Cancer Research*, 6:2876-2880, 2000.
Koshkina et al., "Improved respiratory delivery of the anticancer drugs, camptothecin and paclitaxel with 5% CO2-enriched air: pharmacokinetic studies," *Cancer Chemother. Pharmacol.*, 47:451-456, 2001.
Koshkina et al., "Paclitaxel liposome aerosol treatment induces inhibition of pulmonary metastases in murine renal carcinoma model," *Clinical Cancer Research*, 7:3258-3262, 2001.
Kosmas et al., "Gemcitabine and docetaxel as second-line chemotherapy for patients with nonsmall cell lung carcinoma who fail prior paclitaxel plus platinum-based regimens," *Cancer*, 92:2902-2910, 2001.
Meerum-Terwogt et al., "Coadministration of oral cyclosporin A enables oral therapy with paclitaxel," *Clin. Cancer Res.*, 5:3379-3384, 1999.
Remuzzi and Perico, Cyclosporine-induced renal dysfunction in experimental animals and humans, *Kidney Int. Suppl.*, 52:S70-74, 1995.
Ross et al., "Cyclosporin A enhances paclitaxel toxicity against leukemia and respiratory epithelial cancers," *Clin. Cancer, Res.*, 3:57-62, 1997.
Rowinsky and Donehower, "Paclitaxel (taxol)," *N. Engl. J. Med.*, 332:1004-1014, 1995.

(Continued)

*Primary Examiner*—Karen A. Canella
(74) *Attorney, Agent, or Firm*—Fulbright & Jaworski L.L.P.

(57) ABSTRACT

The present invention provides a method of inhibiting growth of lung metastases in an individual comprising the steps of administering a dose of a lipid-drug enhancer liposomal complex and, in sequence, administering a dose of a lipid-anticancer drug liposomal complex. Furthermore, the lipid-drug enhancer liposomal complex may be administered in a continuing dose with the lipid-anticancer drug liposomal complex whereby both liposomal complexes are mixed in the nebulizer. Methods of inhibiting growth of lung metastases in an individual by the sequential administration via aerosolization of a dilauroylphosphatidylcholine-cyclosporin A liposomal complex and a dilauroylphosphatidylcholine-paclitaxel liposomal complex are also provided.

26 Claims, 4 Drawing Sheets

OTHER PUBLICATIONS

Sakai et al., "A phse II study of paclitaxel plus cisplatin for advanced non-small-cell lung cancer in Japanese patients," *Cancer Chemother. Pharmacol.*, 48:499-503, 2001.

Schiff and Horwitz, "Taxol stabilizes microtubules in mouse fibroblast cells," *Proc. Natl. Acad. Sci. USA*, 77:1561-1565, 1980.

Sharma et al., "Activity of paclitaxel liposome formulations against human ovarian tumor xenografts," *Int. J. Cancer*, 71:103-107, 1997.

Sikic et al., "Modulation and prevention of multidrug resistance by inhibitors of P-glycoprotein," *Cancer Chemother. Pharmacol.*, 40(Suppl):S13-19, 1997.

Sonnichsen et al., "Variability in human cytochrome P450 paclitaxel metabolism," *J. Pharmacol. Exp. Ther.*, 275:566-575, 1995.

Sood et al., "Cyclosporin A reverses chemoresistance in patients with gynecologic malignancies," *Neoplasia*. 1:118-222, 1999.

Sugawara et al., "Lung resistance protein (LRP) expression in human normal tissues in comparison with that of MDR1 and MRP," *Cancer Lett.*, 112:23-31, 1997.

Verschraegen et al., "Clinical Evaluation of the Delivery and Safety of Aerosolized Liposomal 9-Nitro-20(S)-Camptothecin in Patients with Advanced Pulmonary Malignancies," *Clin. Cancer Res.*, 10:2319-2326, 2004.

Wandel et al., "P-glycoprotein and cytochrome P-450 3A inhibition: dissociation of inhibitory potencies," *Cancer Res.*, 59:3944-3948, 1999.

Weiss et al., "Hypersensitivity reactions from taxol," *J. Clin. Oncol.*, 8:1263-1268, 1990.

Yokoyama et al., "Immunohistochemical evidence that P-glycoprotein in non-small cell lung cancers is associated with shorter survival," *Surg. Today*, 29:1141-7, 1999.

Younes et al., "Local tumor irradiation augments the response to IL-2 therapy in a murine renal adenocarcinoma," *Cell Immunol.*, 165:243-251, 1995.

* cited by examiner

AEROSOL DRUG INHIBITION OF LUNG METASTASES

CROSS-REFERENCE TO RELATED APPLICATION

This non-provisional application claims benefit of provisional U.S. Ser. No. 60/381,767, filed May 20, 2002, now abandoned.

BACKGROUND OF THE INVENTION

1. Field of the Invention

This invention relates to the fields of pharmacology and cancer treatment. More specifically, this invention relates to the combination of anticancer drugs with a drug-enhancing agent administered by aerosol for the treatment of lung cancer in vivo.

2. Description of the Related Art

Lung cancer remains the leading cause of cancer-related deaths. Traditional systemic routes of drug delivery have yielded limited results because of the inability to provide effective concentrations at the sites of cancer without encountering dose-limiting toxicity. An aerosol route for immediate administration of various therapeutic agents to the lungs has been described (1-3). Inhalation of liposomal formulations of the lipophilic anticancer drug, 9-nitrocamptothecin (9NC), was found to be effective against human cancer xenografts and experimental pulmonary metastases in mice at the doses significantly lower than used by other routes of administration (2, 4). A phase I clinical trial in patients with pulmonary cancer with 9NC aerosol treatment indicated that this treatment is sufficiently well tolerated for further clinical evaluation (5).

Paclitaxel (PTX) is among the promising anticancer agents for lung cancer therapy; it is a lipophilic agent with a wide spectrum of anticancer activity including refractory lung cancer (6). Its use, however, may be limited by acquired resistance of tumor cells to the drug. Several mechanisms of resistance to taxanes have been reported. The paclitaxel molecule disrupts tubulin dynamics and can cause cell proliferation arrest at G2/M phase (18). Paclitaxel is used extensively for treatment of lung cancer and is effective as a single agent, but also it is effective in combination therapy with other anticancer drugs and radiation (19-21). The drug is administered intravenously in a clinical setting since its bioavailability is poor after oral administration. The drug is currently administered in a mixture of polyoxyethylated castor oil and ethanol (Diluent-12) exclusively by continuous intravenous infusion. Paclitaxel's use has been limited by hypersensitivity reactions to Diluent-12 (7). In clinical studies it was shown that the bioavailability of paclitaxel administered orally increased 9-fold with concurrent administration of cyclosporin (22).

Liposomes were found to improve pharmacological characteristics of paclitaxel and to be less toxic compared to Diluent-12 (8, 9). Inhalation of liposomal formulation of paclitaxel by mice bearing renal carcinoma pulmonary metastases caused significant tumor growth inhibition and prolonged survival of the animals (2). In these experiments, the total inhaled deposited dose of paclitaxel was 6.3 mg/kg, administered 3 times/week. Dose-limiting toxicity was one of the reasons that prevented optimum use of the drug. Another reason could be the possible development of drug resistance by cancer cells.

The main mechanism of paclitaxel-induced resistance is associated with overexpression of plasma membrane glycoprotein (P-glycoprotein) which works as a drug transport protein that decreases intracellular drug concentrations. P-glycoprotein antagonists, including cyclosporins, are being investigated for use in combination with chemotherapeutic agents to enhance the apoptotic effect and to prevent resistance at the target site. In patients with established resistance remissions were observed when cyclosporin A or other cyclosporin was added to therapy, even when with the anticancer drug cytotoxin, the dose was reduced by as much as 3-fold (23).

Cyclosporin A has been successfully used to reverse the resistance of neoplastic cells to paclitaxel in vitro and in vivo (10, 11). However, one limiting factor is that cyclosporin A is a powerful immunosuppressive agent and can cause nephrotoxicity (30). Liposome formulation of cyclosporin A for inhalation have been developed and tested for the treatment of immunologically mediated lung diseases (3). Inhalation of cyclosporin A with the initial concentration of the drug in the nebulizer at 5 mg/ml during 30-45 min of inhalation was demonstrated to be safe for humans and rodents (3, 31).

Cyclosporins have a high-affinity binding capacity with P-glycoprotein. Competing with other drugs (taxanes, anthracyclines, epipodophyllotoxins, etc.) for binding with P-glycoprotein, cyclosporin A may prevent the active extrusion of these cytotoxic drugs from tumor cells (24, 25). Cyclosporin A is also known as an inhibitor of cytochrome P450-mediated (CYP) metabolism thereby inhibiting cytochrome P450-mediated first pass metabolism of paclitaxel (26). The main enzymes, CYP2C8 and CYP3C4, involved in paclitaxel metabolism belong to the P450 family and are expressed in the respiratory tissues (12, 13). These isoenzymes metabolize paclitaxel to 6α-hydroxypaclitaxel and 3β-hydroxypaclitaxel, respectively (12, 27).

P-glycoprotein and other resistance-associated proteins are expressed in normal human pulmonary tissue (28). In one study more than 60% of patients with non-small cell lung carcinoma were found to be positive for P-glycoprotein and 5-year survival rate of P-glycoprotein positive patients was significantly lower compared with those without P-glycoprotein (29). Moreover, the expression of the CYP3A4 gene was induced by administration of paclitaxel in lung cancer patients and the level of CYP2C expression in samples of lung cancer was significantly higher than in the normal lung tissue (13).

The prior art is deficient in the lack of a method of inhibiting the growth of pulmonary tumors. More specifically, the prior art lacks methods for the chemotherapeutic treatment of lung cancer in vivo via aerosol administration of anticancer drugs with cyclosporin A. The present invention fulfills this longstanding need and desire in the art.

SUMMARY OF THE INVENTION

The present invention is directed to method of inhibiting growth of lung metastases in an individual. A dose of a lipid-drug enhancer liposomal complex is administered to the individual and, in sequence, a dose of a lipid-anticancer drug liposomal complex is administered to the individual. Both of the liposomal complexes are delivered via aerosolization from a nebulizer whereby the drug enhancer and the anticancer drug inhibit growth of lung metastases in the individual.

The present invention also is directed to the method of inhibiting growth of lung metastases in an individual described supra where a dilauroylphosphatidylcholine-cyclosporin A liposomal complex is the lipid-drug enhancer liposomal complex and a dilauroylphosphatidylcholine-paclitaxel liposomal complex is the lipid-anticancer drug complex.

The present invention is directed further to another method of inhibiting growth of lung metastases in an individual. First a dose of a dilauroylphosphatidylcholine-cyclosporin A liposomal complex is administered to the individual via aerosolization from a nebulizer. Then, in sequence, a dose of a dilauroylphosphatidylcholine-paclitaxel liposomal complex is administered while concurrently administering a continuing dose of the dilauroylphosphatidylcholine-cyclosporin A liposomal complex via aerosolization from a nebulizer where the dilauroylphosphatidylcholine-cyclosporin A liposomal complex is mixed with the dilauroylphosphatidylcholine-paclitaxel liposomal complex in the nebulizer. The drug enhancer and of the anticancer drug inhibit growth of lung metastases in the individual.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized. Details of the above may be had by reference to certain embodiments thereof which are illustrated in the appended drawings. These drawings form a part of the specification. It is to be noted; however, that the appended drawings illustrate preferred embodiments of the invention and therefore are not to be considered limiting in their scope.

DETAILED DESCRIPTION OF THE INVENTION

Figure 1A:
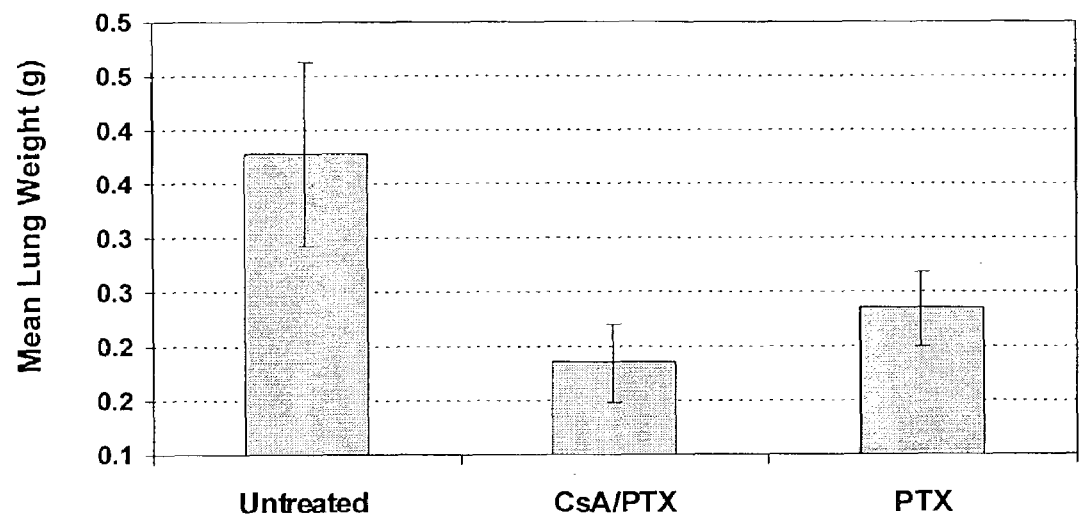
FIGS. 1A-1B show the effect of concurrent administration of cyclosporin A with paclitaxel on Renca pulmonary metastatic growth in BALB/c mice. Mice were injected into tail veins with 100,000 Renca cells/mouse. Cyclosporin A was inhaled for 30 min before paclitaxel administration, 3 times weekly for 3 weeks starting 24 hrs after tumor inoculation. Therapeutic activity of treatments was estimated by lung weights (FIG. 1A) and tumor area (FIG. 1B) measurements.

In one embodiment of the present invention there is provided a method of inhibiting growth of lung metastases in an individual comprising the steps of administering a dose of a lipid-drug enhancer liposomal complex and, in sequence, administering a dose of a lipid-anticancer drug liposomal complex where both of the liposomal complexes are delivered via aerosolization from a nebulizer whereby the drug enhancer and the anticancer drug inhibit growth of lung metastases in the individual. The administration sequence steps maybe repeated at least once.

In all aspects of this embodiment the drug enhancing agents may be cyclosporin A, cyclosporin D, verapamil, ketoconazole, PCS 833, erythromycin, nifedipine, rapamycin or mibefradil. Representative examples of the anticancer drugs are paclitaxel, doxirubicin, etoposide, vinblastine, camptothecins, cisplatinum, carboplatinum, daunorubicin, or adriamycin. The liposome may have a transition temperature of less than about 17° C. A representative example of such a liposome is dilauroylphosphatidylcholine. The aerosol may comprise about 5% to about 10% carbon dioxide in air.

In one aspect the dose of the lipid-drug enhancer complex is a dose of dilauroylphosphatidylcholine-cyclosporin A liposomal complex. Cyclosporin A may be administered in a dose comprising a concentration of about 5.0 mg cyclosporin A/ml solution in the nebulizer at a cyclosporin A: dilauroylphosphatidylcholine weight ratio of about 1:7.5. In a related aspect the dose of the lipid-anticancer drug liposomal complex is a dose of dilauroyl phosphatidylcholine-paclitaxel liposomal complex. Paclitaxel may be administered in a dose comprising about 10.0 mg paclitaxel/ml solution in the nebulizer at a paclitaxel:dilauroylphosphatidylcholine weight ratio of about 1:10.

This embodiment further comprises the step of concurrently administering a continuing dose of the lipid-drug enhancer liposomal complex with the lipid-anticancer drug complex via aerosolization from a nebulizer where the lipid-drug enhancer liposomal complex is mixed with the lipid-anticancer drug complex in the nebulizer. As stated supra the dose of lipid-drug enhancer complex is a dose of a dilauroylphosphatidylcholine-cyclosporin A liposomal complex. Prior to mixing in the nebulizer the concentration of cyclosporin A and the liposomal complex weight ratio in the dose administered are as described supra. Again, as stated supra, the dose of lipid-anticancer drug complex is a dose of a dilauroylphosphatidylcholine-paclitaxel liposomal complex. Prior to mixing in the nebulizer the concentration of paclitaxel and the liposomal complex weight ratio in the dose administered are as described supra.

In another embodiment of the present invention, there is provided a method of inhibiting growth of lung metastases in an individual comprising the steps of administering a dose of a dilauroylphosphatidylcholine-cyclosporin A liposomal complex; and, in sequence, administering a dose of a dilauroylphosphatidylcholine-paclitaxel liposomal complex where both of the liposomal complexes are delivered via aerosolization from a nebulizer whereby cyclosporin A and paclitaxel inhibit growth of lung metastases in the individual. The administration sequence steps may be repeated at least once. In this embodiment the dose concentration and the weight ratios of the liposomal complexes of the cyclosporin A and paclitaxel in the nebulizer are as disclosed supra.

In yet another embodiment of the present invention there is provided a method of inhibiting growth of lung metastases in an individual comprising the steps of administering a dose of a dilauroylphosphatidylcholine-cyclosporin A liposomal complex via aerosolization from a nebulizer and, in sequence, administering a dose of a dilauroylphosphatidylcholine-paclitaxel liposomal complex while concurrently administering a continuing dose of the dilauroylphosphatidylcholine-cyclosporin A liposomal complex via aerosolization from a nebulizer where the dilauroylphosphatidylcholine-cyclosporin A liposomal complex is mixed with said dilauroylphosphatidylcholine-paclitaxel liposomal complex in the nebulizer whereby cyclosporin A and paclitaxel inhibit growth of lung metastases in the individual.

In this embodiment the sequential and concurrent administration steps may be repeated at least once. Furthermore the dose concentration and the weight ratio of the liposomal complexes, of cyclosporin A in the nebulizer for the first adminstration of the dilauroylphosphatidylcholine-cyclosporin A liposomal complex and prior to mixing in the nebulizer for the continuing adminstration with the dilauroylphosphatidylcholine-paclitaxel liposomal complex are as disclosed supra. Also, the dose concentration and the weight ratio of the liposomal complex of paclitaxel in the nebulizer are as disclosed supra.

The following definitions are given for the purpose of facilitating understanding of the inventions disclosed herein. Any terms not specifically defined should be interpreted according to the common meaning of the term in the art.

As used herein, the term "individual" shall refer to animals and humans.

As used herein, the term "anti-cancer drug" shall refer to those drugs with a high probability of causing multidrug-type related resistance during therapy for pulmonary malignancies.

As used herein, the term "drug-enhancer" shall refer to those therapeutic agents that when delivered in combination with the anticancer drug via aerosol enhance or increase the therapeutic effectiveness of the anticancer drug.

The following abbreviations may be used herein:

Cyclosporin A: CsA; paclitaxel: PTX; multiple drug resistance: MDR; cytochrome P450-mediated: CYP; plasma membrane glycoprotein; P-glycoprotein or P-gp.

The present invention provides a method of aerosol co-administration of an anticancer drug, preferably paclitaxel, with a drug-enhancing agent such as cyclosporin A for lung cancer therapy in vivo. Both the drug and the drug-enhancing agent are encapsulated into liposomal formulations and administered via aerosol to BALB/c mice bearing pulmonary renal carcinoma metastases. The lipid in the liposome may be a lipid having a transition temperature of 17° C. or less, for example dilauroylphosphatidylcholine. The liposomal complex may also be delivered via an aerosol comprising about 5% to about 10% carbon dioxide in air.

Particularly, two regimens of combination treatment are provided. In the first combination group cyclosporin A is administered as a liposome aerosol for one half hour before starting one half hour treatment with PTX liposome aerosol (CsA/PTX). In the second group cyclosporin A liposome aerosol is administered for one half hour prior to paclitaxel and then a cyclosporin A liposomal aerosol is concurrently administered with a paclitaxel liposomal aerosol for an additional hour (CsA/PTX+CsA). Animals receiving no treatment or being treated with aerosolized paclitaxel only are used as controls.

In the CsA/PTX+CsA combination, aerosolization of PTX+CsA is accomplished by mixing the liposomal paclitaxel with the liposomal CsA in the nebulizer prior to aerosolization of the combination. Cyclosporin A may be administered in a dose comprising, although not limited to, about 5.0 mg cyclosporin A/ml of solution in suspension prior to nebulization. Paclitaxel may be administered in a dose comprising, although not limited to, about 10.0 mg paclitaxel/ml solution in suspension prior to nebulization at a paclitaxel:dilauroylphosphatidylcholine weight ratio of about 1:10.

For concurrent CsA+paclitaxel administration the nebulizer volume is doubled, so the concentrations of CsA and paclitaxel per total solution volume in the nebulizer is halved, i.e. about 5.0 mg CsA/ml and about 2.5 mg paclitaxel/ml, respectively. However, administration time is doubled so the amount of aerosolized dose is the same as if the CsA and paclitaxel liposomal complexes were aerosolized individually. The total dose of paclitaxel remains the same in all groups whereas the cyclosporin A dose doubles in the cyclosporin A/paclitaxel-cyclosporin A group. These doses may be reduced if toxicity is detected for either drug. One of ordinary skill in the art can determine an appropriate lower dose without undue experimentation.

Both combination aerosol treatments were more effective compared with single-agent paclitaxel aerosol treatment. The dose escalation of cyclosporin A increased inhibitory activity of paclitaxel on lung cancer growth in mice. The most effective regimen was that for mice that inhaled cyclosporin A prior to paclitaxel administration and continued to inhale cyclosporin A during paclitaxel treatment (CsA/paclitaxel-CSA). In this group the number of tumor lesions and the size of the tumors were significantly reduced compared with the group receiving CsA/paclitaxel treatment or paclitaxel only.

In the CsA/PTX-CSA group, escalation of the cyclosporin A dose caused increased toxicity, as demonstrated by a ~15% whole body weight loss, after 2 weeks of treatment compared with other treated groups, where total body weight was decreased by 6%. The toxicity was quickly reversed after the treatment had been stopped. Histopathology analysis of lung tissues obtained from mice receiving a single dose of cyclosporin A prior to paclitaxel 3 times per week for 3 weeks did not show a significant pulmonary inflammatory response to the treatment. This indicates that the observed toxicity evaluated by the whole body weight loss was systemic.

It is contemplated that liposomal aerosol cyclosporin A can be used as an adjuvant with other MDR-related anti-cancer drugs having a high probability of causing the multidrug-type resistance, e.g., doxorubicin, etoposide vinblastine, camptothecins, cisplatinum, carboplatinum, daunorubicin, and adriamycin, for the therapy of pulmonary malignancies. As systemic toxicity may be a consideration in using cyclosporin A in such combinations for aerosol therapeutic treatment, it is further contemplated that the P-glycoprotein inhibitors having a lower toxicity index may be used for alternative combinations. A liposomal complex comprising an anti-cancer drug and a drug enhancing agent such as verapamil, ketoconazole, PCS 833, erythromycin, nifedipine, cyclosporin D, rapamycin or mibefradil may be used. These drugs have similar effects on the P450 cytochrome family enzymes and P-glycoprotein which all participate in metabolism.

The following examples are given for the purpose of illustrating various embodiments of the invention and are not meant to limit the present invention in any fashion. The statistical significance of difference between groups in the examples given below was calculated by Student t-test, two-tailed. P values <0.05 were considered to be statistically significant.

EXAMPLE 1

Chemicals

Paclitaxel was obtained from SuperGen (San Ramon, Calif.). Cyclosporin A was purchased from Chemwerth (Woodridge, Conn.). Dilauroylphosphatidylcholine (DLPC) was purchased from Avanti Polar Lipids (Alabaster, Ala.). Organic solvents (HPLC grade) were obtained from Fisher Scientific. Sterile water for irrigation was purchased from Baxter Healthcare Corporation (Deerfield, Ill.).

EXAMPLE 2

Animals

Female BALB/c mice (7-8 weeks old) were obtained from Harlan-Sprague Dawley (Indianapolis, Ind.) and housed in standard cages with food and water provided ad libitum. Experiments were performed with the approval of the Institutional Animal Care and Use Committee.

EXAMPLE 3

Cell Culture and Animal Model

The mouse renal carcinoma cell line (Renca) was provided by and maintained by serial passages as described by Dr. Robert Wiltrout, National Cancer Institute (Frederick, Md.). Prior to in vivo implantation, Renca cells were cultured in vitro for 2 passages as described previously (14). To induce pulmonary metastases, 100,000 cells were injected intravenously in 0.2 ml saline via tail vein in syngeneic BALB/c mice.

EXAMPLE 4

Preparation of Liposomal Formulations of Paclitaxel and Cyclosporin A

Figure 1B:
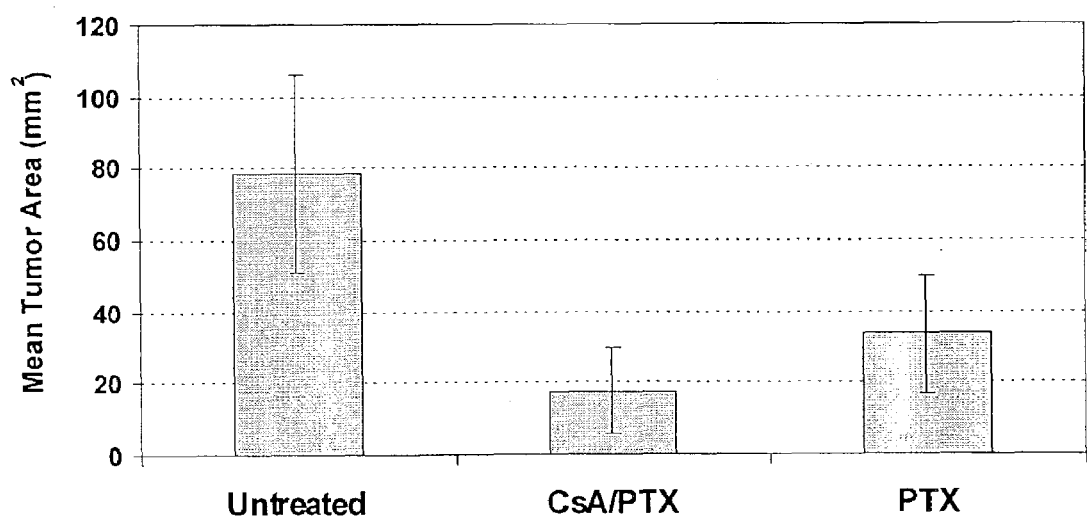

Liposome formulations were prepared as described previously for paclitaxel (15) and cyclosporin A (3). Briefly, stock solutions of dilauroylphosphatidylcholine and drugs were prepared in t-butanol. Aliquots of paclitaxel and dilauroylphosphatidylcholine (1:10 w/w) or cyclosporin A and dilauroylphosphatidylcholine (1:7.5 w/w) were mixed, frozen at −70° C. and lyophilized overnight to dryness. Before use the mixture was reconstituted with sterile water and vortexed until a homogeneous multi-lamellar liposomal suspension was obtained. The initial concentration of paclitaxel and cyclosporin A in suspension prior to nebulization was 10 and 5 mg/ml, respectively. The aerosol characteristics of these formulations are described elsewhere (15, 16).

EXAMPLE 5

Aerosol Drug Delivery

The treatment of mice bearing pulmonary tumors with aerosol was performed as previously described (15, 17). Briefly, an AERO-MIST jet nebulizer (CIS-USA, Bedford, Mass.) was used to generate aerosol particles at the air flow rate of 10 L/min. Mice were placed in a sealed plastic cage unrestricted and exposed to aerosol. The aerosol was generated with 5% $CO_2$-enriched air obtained by mixing normal air and $CO_2$ with a blender (Bird 3M, Palm Springs, Calif.) and the $CO_2$ concentrations were calibrated with a Fluid Fyrite (Bacharach Inc., Pittsburgh, Pa.). The utilization of carbon dioxide increased pulmonary deposition of the drugs approximately 3-4 fold (15).

The deposited dose of PTX/DLPC aerosol given with cyclosporin A is calculated as follows: a 25 gm mouse has an inhaled minute volume of 1 cc/min/gm, or 25 cc per mouse, and 25/1000×175 μg of PTX/l of aerosol=4.38 μg of PTX inhaled/mouse/min. This value x 0.3, i.e., fraction of inhaled dose deposited, or 1.3 mg/mouse/min×20 min=39.375 μg deposited/mouse in 30 minutes×5.7 increased deposition due to 5% CO2 in inspired air=224 μg retained dose in 25 gm mouse in 30 minutes or 9.0 mg/kg.

EXAMPLE 6

In Vivo Antitumor Activity

BALB/c mice were injected with 100,000 Renca cells into tail vein on day 0. On day 1, they were randomly divided into groups of 10 mice. One group of mice was left untreated, the second group of mice received paclitaxel-only treatment, the third group inhaled cyclosporin A for 30 minutes, which was immediately followed by paclitaxel inhalation for another 30 minutes (cyclosporin A/paclitaxel). The fourth group inhaled cyclosporin A for 30 min prior to paclitaxel, followed by a 60 min dose of combined cyclosporin A and paclitaxel (2.5 and 5 mg/mL final concentration, respectively) after treatment with paclitaxel, which extended the total treatment up to 90 minutes (cyclosporin A/paclitaxel+cyclosporin A). For the combination paclitaxel+cyclosporin A were mixed together in the nebulizer in separate liposomal complexes. In this instance the volumes of the complexes in solution were equal.

Mice were treated 5 days a week for 3 weeks. During treatment mice were weighed twice weekly. At the end of three weeks they were sacrificed by exposure to Isoflurane, USP and exsanguination. Lungs were resected and weighed. The lungs were fixed subsequently in the Bovin's fixative for tumor enumeration and sizing. One mouse selected for frequent tumors and one selected for none or few tumors were removed for other purposes from each experimental group and were not considered in the evaluation presented in Table 2 below.

EXAMPLE 7

Histology

Mice received the aerosol treatment with cyclosporin A-paclitaxel as described above for 3 consecutive weeks. Mice were sacrificed 24 after the last treatment. Lungs were isolated, cannulated and fixed by inflation of 10% neutral buffered formalin (NBF), embedded in paraffin and processed for histological analysis. Sections were cut at 5 μm, stained with hematoxylin and eosin, and examined under the light microscope. Lungs from untreated animals were used as negative control.

EXAMPLE 8

Antitumor Effect of Different Combination of Paclitaxel and Cyclosporin A Aerosol Treatments Three groups of ten mice were inoculated with renca cells, one groups served as controls, one group was given an aerosol containing PTX and one group was given aerosol containing CsA/PTX. FIG. 1A shows the response to treatment based on changes in lung weights. Both treated groups had highly significantly lower lung weights than controls (P<0.001) and mice receiving CsA/paclitaxel aerosol had highly significantly lower lung weights than those treated with paclitaxel only. Tumor areas in these animals showed an almost identical pattern of response with highly significantly smaller tumor surface areas in treated animals compared to controls and significantly smaller tumor surface areas in the CsA/paclitaxel treated animals compared to paclitaxel treated animals (FIG. 1B).

Renca murine carcinoma cells ($1\times10^5$/0.2 ml) were inoculated intravenously. Treatment was started the next day. Mice inhaled liposome CsA for 30 min, which was immediately followed by 30-min inhalation of liposome paclitaxel, 3 times weekly. After 25 days mice were sacrificed, lungs were resected and tumor lesions counted and measured. The tumor area for both treated groups was lower than in untreated group (P<0.05, two-tailed t test) as shown in Table 1.

TABLE 1

Effect of Aerosol Combination of Paclitaxel with Cyclosporin A Treatment on Pulmonary Metastases Growth in Mice

| Treatment | Mean Tumor Number ± SD | Mean Tumor Area ± SD (mm$^2$) |
|---|---|---|
| Untreated (n = 13) | 44 ± 16 | 39.3 ± 22.9 |
| PTX (n = 11) | 45 ± 15[a] | 24.1 ± 8.7[b] |
| CsA/PTX (n = 11) | 29 ± 14[a] | 16.4 ± 7.4[b,d] |

[a]P > 0.05 compared with untreated group. [b]P ≤ 0.04 compared with untreated group. [c]P = 0.04 compared with paclitaxel group.

In a second experiment the tumors grew more slowly than in the first experiment and the lung weights were not significantly different. The number of tumors, as enumerated in Table 1 and shown in FIG. 2, in both treated groups was not significantly decreased over the untreated group, but the mean tumor area was smaller in paclitaxel and CsA/PTX groups (P<0.04), respectively, compared to the untreated group. The tumor area for the CsA/PTX treated group was less than the tumor area for the paclitaxel-treated groups (P=0.04).

Figure 2:
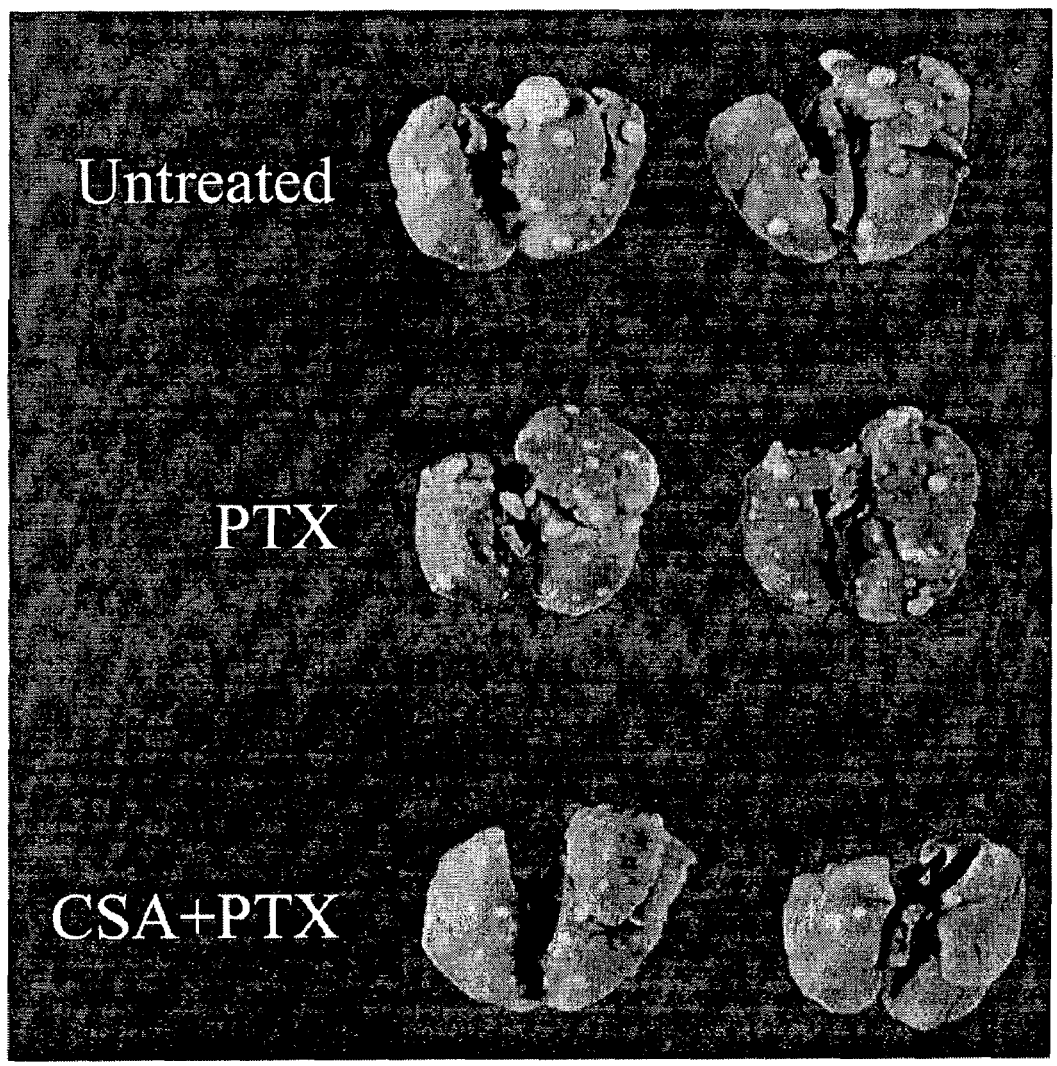
FIG. 2 depicts lungs of mice treated three times weekly for three weeks via treatment as shown in Table 1. Note smaller and fewer tumors progressively, i.e., untreated >PTX >CsA/PTX.

In the third experiment, one more combination, a CsA/PTX+CsA group, was added, as enumerated in Table 2 and shown in FIG. 2. The increase of the CsA dose by administration of CsA mixed with PTX for 60-minute periods of treatment improved the therapeutic effect, despite the need to discontinue its use after 2 weeks due to toxicity. The other groups, i.e., CsA/PTX and PTX-only, were treated continuously for 3 weeks. As measured by tumors visible on lung surfaces with a low power microscope both combination regimens resulted in significantly fewer tumors than control animals and animals receiving PTX-only. However, tumor volumes of all three treated groups were not significantly different from the control group. The doubled dosage of CsA was manifested by a significantly reduced number of tumors and reduced tumor volumes compare to the use of only one dosage period with CsA. Moreover, both CsA combinations were highly significantly better with repect to both tumor numbers and tumor volumes than paclitaxel alone.

TABLE 2

Anticancer Aerosol Treatment With Cyclosporin A before PTX and before and during PTX Compared to PTX-Only and to No Treatment

| Treatment | Mean Tumor Number ± SD | Mean Tumor Volume ± SD (mm$^3$) |
|---|---|---|
| Untreated | 9.1 ± 5.8 | 11.6 ± 16 |
| PTX only | 11.9 ± 5.2 | 5.5 ± 3.6 |
| CsA/PTX | 2.7 ± 2.1 | 0.7 ± 0.6 |
| CsA/PTX + CsA | 0.8 ± 0.9 | 0.2 ± 0.2 |
| Control versus | | |
| PTX | 0.336 | 0.311 |
| CsA/PTX | 0.016 | 0.097 |
| CsA/PTX + CsA | 0.0001 | 0.063 |
| CsA:PTX versus CsA/PTX + CsA | 0.029 | 0.032 |
| PTX versus CsA/PTX | 0.001 | 0.004 |
| CsA/PTX + CsA | <0.001 | |

EXAMPLE 9

Figure 3:
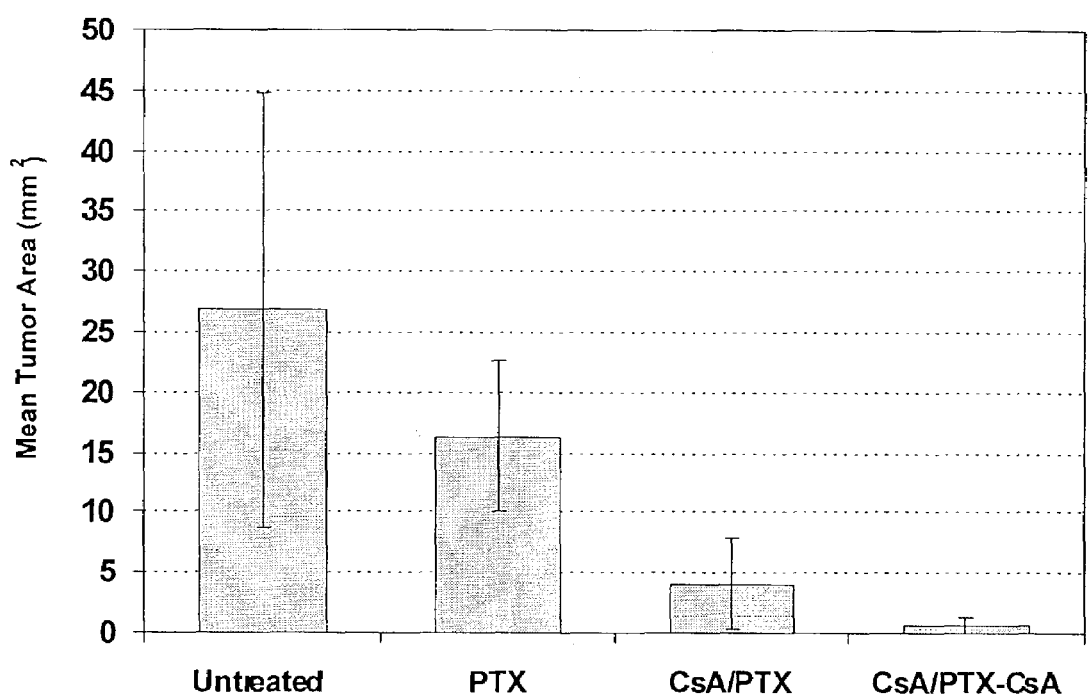
FIG. 3 depicts body weights of mice during three weeks of treatment with PTX, CsA/PTX and CsA/PTX+CsA compared to untreated controls. CsA/PTX+CsA-treated mice weighed significantly less than untreated controls on days 9, q4, 19 and 22. CsA/PTX+CsA-treated mice weighted significantly less than the paclitaxel ($P<0.05$) and PTX/CsA-treated mice on days 9 and 14. Paclitaxel and CsA/paclitaxel treated groups weighed significantly less than untreated controls on days 19 and 22 ($P<0.01$ except where noted).
Figure 4A:
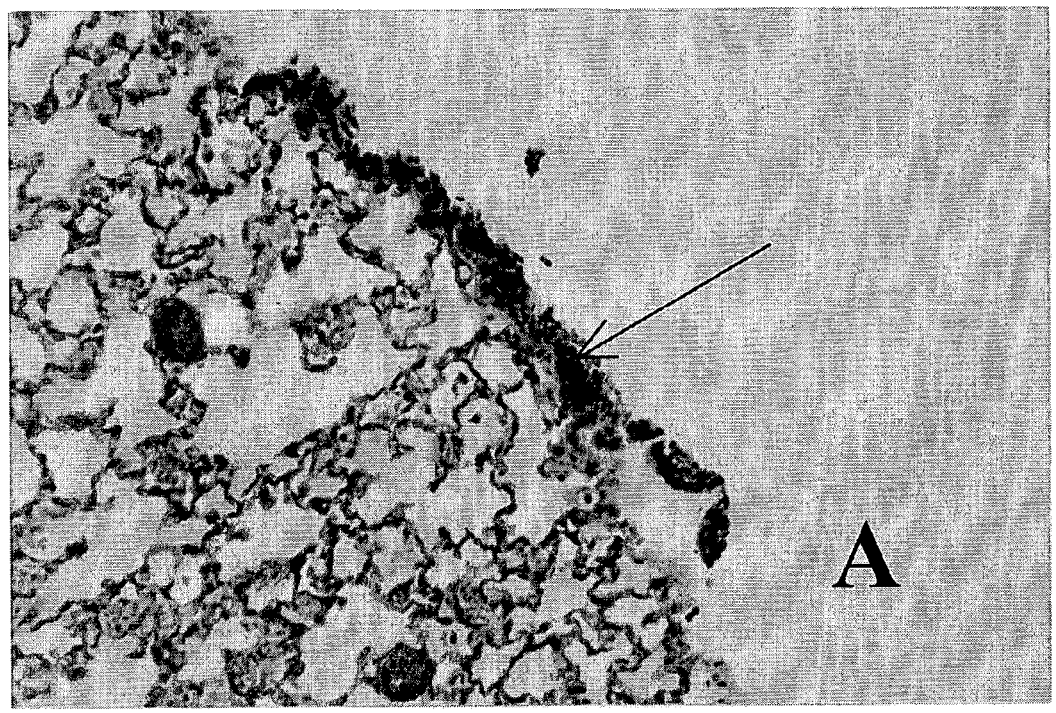
FIGS. 4A-4B are histological sections of non-cancerous BALB/c mice treated with aerosol cyclosporin A/paclitaxel combination. Mice (n=4) received treatment 3 times per week for 3 weeks. Only one mouse showed limited lymphocytes aggregation on the pleural surface (FIG. 4A, arrow), whereas the rest of the pulmonary tissue and lungs of three other mice showed no evidence for inflammatory response (FIG. 4B).
Figure 4B:
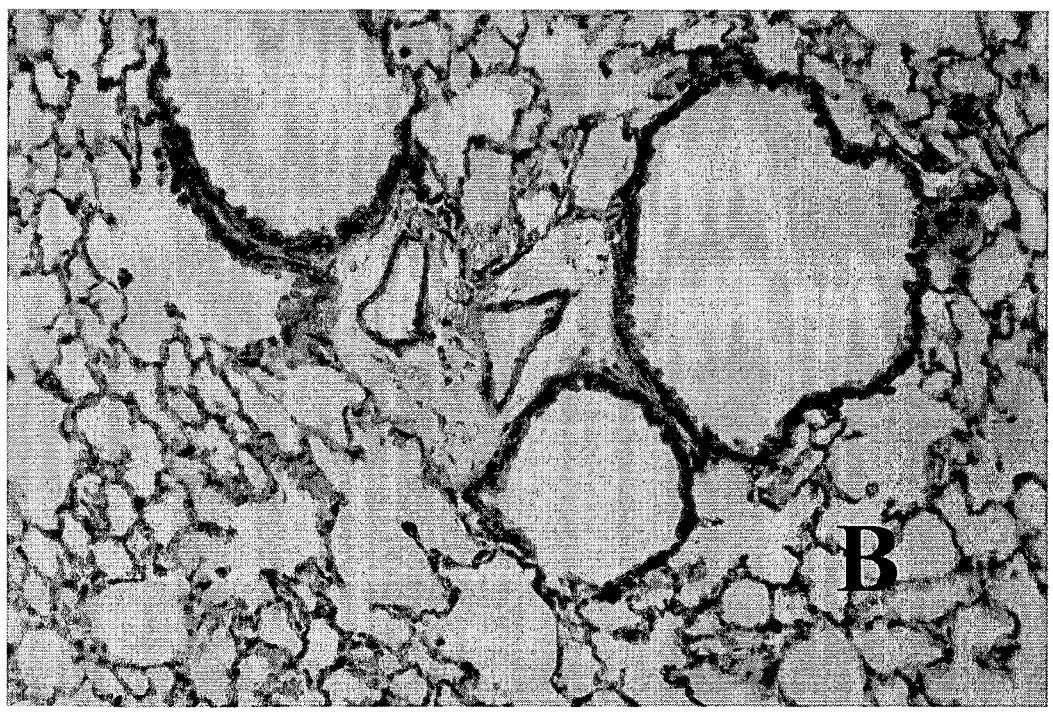

Toxicity Studies for Different Regimens of Cyclosporin A and Paclitaxel Combination Treatments Administered by Aerosol Toxicity of the treatment was examined by comparison of the whole body weights as shown in FIG. 3. The body weight of mice treated with CsA/PTX+CsA decreased significantly by day 9 and remained so through day 22, although treatment was stopped at day 14 and some weight was regained. The other two treated groups lost some weight by day 9 but reached a significant reduction compred to the control group only at days 19 and 22. Treatment was never discontinued in these latter groups. Histopathological examination was performed on representative mice of the CsA/PTX group and no significant lesions were noted. After examination of the pulmonary sections under the microscope only in one mouse local infiltration of leukocytes was detected on the pleural surface (FIG. 4A). There were no signs of inflammation or tissue damage in the lungs of other treated mice (FIG. 4B).

The following references are cited herein:
1. Koshkina, N. V., Kleinerman, E. S., Waldrep, J. C., Jia, S. F., Worth, L. L., Gilbert, B. E., and Knight, V. 9-Nitrocamptothecin liposome aerosol treatment of melanoma and osteosarcoma lung metastases in mice. Clin. Cancer Res., 6: 2876-2880, 2000.
2. Koshkina, N. V., Waldrep, J. C., Roberts, L. E., Golunski, E., Melton, S., and Knight, V. Paclitaxel liposome aerosol treatment induces inhibition of pulmonary metastases in murine renal carcinoma model. Clin. Cancer Res., 7: 3258-3262, 2001.
3. Gilbert, B E, Knight, C., Alvarez, F. G., Waldrep, C., Rodarte, J. R., Knight, V., and Eschenbache, W. L. Tolerance of volunteers to cyclosporine A-dilauroylphosphatidylcholine liposome aerosol. Am. J. Respir. Crit. Care Med., 156: 1789-1793, 1997.
4. Knight, V., Koshkina, N. V., Waldrep, J. C., Giovanella, B. C., and Gilbert, B. E. Anticancer effect of 9-nitrocamptothecin liposome aerosol on human cancer xenografts in nude mice. Cancer Chemother. Pharmacol., 44: 1771-86, 1997

5. Verschraegen, C. F., Gilbert, B. E., Huaringa, A. J., Newman, R., Harris, N., Leyva, F. J, Keus, L., Campbell, K., Nelson-Taylor, T., and Knight, V. Feasibility, phase I, and pharmacological study of aerosolized liposomal 9-nitro-20(S)-camptothecin in patients with advanced malignancies in the lungs. Ann. N.Y. Acad. Sci., 922: 352-354, 2000.
6. Rowinsky, E. K., and Donehower, R. C. Paclitaxel (taxol). N. Engl. J. Med., 332: 1004-1014, 1995.
7. Weiss, R. B., Donehower, R. C., Wiernik, P. H., Ohnuma, T., Gralla, R. J., Trump, D. L., Baker, J. R., van Echo, D. A., von Hoff, D. D., and Leyland-Jones, B. Hypersensitivity reactions from taxol. J. Clin. Oncol., 8: 1263-1268, 1990.
8. Sharma, A., Mayhew, E., Bolcsak, L., Cavanaugh, C., Harmon, P., Janoff, A., and Bernacki, R. J. Activity of paclitaxel liposome formulations against human ovarian tumor xenografts. Int. J. Cancer, 71: 103-107, 1997.
9. Cabanes, A., Briggs, K. E., Cokhale, P. C., Treat, J. A., and Rahman, A. Comparative in vivo studies with paclitaxel and liposome-encapsulated paclitaxel. Int. J. Oncol., 12: 1035-1040, 1998.
10. Ross, H. J., Canada, A. L., and Slater, L M. Cyclosporin A enhances paclitaxel toxicity against leukemia and respiratory epithelial cancers. Clin. Cancer. Res., 3: 57-62, 1997.
11. Sood, A. K., Sorosky, J. I., Squatrito, R. C., Skilling, J. S., Anderson, B., and Buller, R. E. Cyclosporin A reverses chemoresistance in patients with gynecologic malignancies. Neoplasia. 1:118-122, 1999.
12. Sonnichsen, D. S., Liu, Q., Schuetz, E. G., Schuetz, J. D., Pappo, A., and Relling, M. V. Variability in human cytochrome P450 paclitaxel metabolism. J. Pharmacol. Exp. Ther., 275: 566-575, 1995.
13. Fujitaka, K., Oguri, T., Isobe, T., Fujiwara, Y., and Kohno, N. Induction of cytochrome P450 3A4 by docetaxel in peripheral mononuclear cells and its expression in lung cancer. Cancer Chemother. Pharmacol., 48: 42-46, 2001.
14. Younes, E., Haas, G. P., Dezso, B., Ali, E., Maughan, R. L., Kukuruga, M. A., Montecillo, E., Pontes, J. E., and Hillman, G. G. Local tumor irradiation augments the response to IL-2 therapy in a murine renal adenocarcinoma. Cell Immunol., 165: 243-251, 1995.
15. Koshkina, N. V., Knight, V., Gilbert, B. E., Golunski, E., Roberts, L., and Waldrep, J. C. Improved respiratory delivery of the anticancer drugs, camptothecin and paclitaxel with 5%CO2-enriched air: pharmacokinetic studies. Cancer Chemother. Pharmacol., 47: 451-456, 2001.
16. Gilbert, B. E., Wilson, S. Z., Garcon, N. M., Wyde, P. R., and Knight, V. Characterization and administration of cyclosporine liposomes as a small-particle aerosol. Transplantation, 56: 974-977, 1993.
17. Knight, V., Koshkina, N. V., Waldrep, J. C., Giovanella, B. C., and Gilbert, B. E. Anticancer effect of 9-nitrocamptothecin liposome aerosol on human cancer xenografts in nude mice. Cancer Chemother. Pharmacol., 44: 177-86, 1999.
18. Schieff, P. B., and Horwitz, S. B. Taxol stabilizes microtubules in mouse fibroblast cells. Proc. Natl. Acad. Sci. USA, 77: 1561-1565, 1980.
19. Sakai, H., Yoneda,S., Tamura, T., Nishiwaki, Y., Yokoyama, A., Watanabe, K., and Saijo, N. A phase II study of paclitaxel plus cisplatin for advanced non-small-cell lung cancer in Japanese patients. Cancer Chemother. Pharmacol., 48: 499-503, 2001.
20. Kosmas, C., Tsavaris, N., Vadiaka, M., Stavroyianni, N., Koutras, A., Malamos, N., Onyenadum, A., Rokana, S., Polyzos, A., and Kalofonos, H. P. Gemcitabine and docetaxel as second-line chemotherapy for patients with nonsmall cell lung carcinoma who fail prior paclitaxel plus platinum-based regimens. Cancer. 92: 2902-2910, 2001
21. Choy, H., and MacRae, R. The current state of paclitaxel and radiation in the combined-modality therapy of non-small cell lung cancer. Semin, Oncol., 28(Suppl 14):17-22, 2001.
22. Meerum-Terwogt, J. M., Malingre, M. M., Beijnen, J. H., ten Bokkel Huinink, W. W., Rosing, H., Koopman, F. J., van Tellingen, O., Swart, M., and Schellens, J. H. Coadministration of oral cyclosporin A enables oral therapy with paclitaxel. Clin. Cancer Res., 5: 3379-3384, 1999.
23. Sikic, B. I., Fisher, G. A., Lum, B. L., Halsey, J., Beketic-Oreskovic, L., and Chen, G. Modulation and prevention of multidrug resistance by inhibitors of P-glycoprotein. Cancer Chemother. Pharmacol., 40 (*Suppl*): S13-19, 1997.
24. Germann, U. A. Detection of recombinant P-glycoprotein in multidrug resistant cultured cells. Mol. Biotechnol., 14: 131-145, 2000.
25. Gottesman, M. M., and Pastan, I. Biochemistry of multidrug resistance mediated by the multidrug transporter. Annu. Rev. Biochem., 62: 385-427, 1993.
26. Wandel, C., Kim, R. B., Kajiji, S., Guengrich, F. P., Wilkinson, G. R., and Wood, A. J. J. Cancer Res., 59: 3944-3948, 1999.
27. Cresteil, T., Monsarrat, B., Alvinerie, P., Treluyer, J. M., Vieira, I., and Wright, M. Taxol metabolism by human liver microsomes: identification of cytochrome P450 isozymes involved in its biotransformation. Cancer Res., 54: 386-392, 1994.
28. Sugawara, I., Akiyama, S., Scheper, R. J., and Itoyama, S. Cancer Lett., 112: 23-31, 1997.
29. Yokoyama, H., Ishida, T., Sugio, K., Inoue, T., and Sugimachi, K. Surg. Today. 29:1141-7, 1999.
30. Remuzzi, G., and Perico, N. Cyclosporine-induced renal dysfunction in experimental animals and humans. Kidney Int. Suppl. 52:S70-74, 1995.
31. Gilbert, et al., Inhalation Toxicology. 9: 717-730, 1997.

Any patents or publications mentioned in this specification are indicative of the levels of those skilled in the art to which the invention pertains. Further, these patents and publications are incorporated by reference herein to the same extent as if each individual publication was indicated to be incorporated specifically and individually by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inhibiting growth of lung metastases in an individual comprising the steps of:
administering a dose of a lipid-drug enhancer liposomal complex; and, in sequence, administering a dose of a lipid-anticancer drug liposomal complex, both of said liposomal complexes delivered via aerosolization from a nebulizer; whereby said drug enhancer and said anticancer drug inhibit growth of lung metastases in the individual.

2. The method of claim 1, wherein the sequential administration of said liposomal complexes is repeated at least once.

3. The method of claim 1, wherein said drug enhancer is cyclosporine A, cyclosporine D, verapamil, ketoconazole, PCS 833, erythromycin, nifedipine, rapamycin or mibefradil.

4. The method of claim 1, wherein said anti-cancer drug is paclitaxel, etoposide, vinblastine, camptothecin, cisplatinum, carboplatinum, daunorubicin, or adriamycin.

5. The method of claim 1, wherein said lipid has a transition temperature of about 17° C. or less.

6. The method of claim 1, wherein said lipid is dilauroylphosphatidylcholine (DLPC).

7. The method of claim 1, wherein said aerosol comprises about 5% to about 10% carbon dioxide.

8. The method of claim 1, wherein said dose of said lipid-drug enhancer complex is a dose of a dilauroylphosphatidylcholine-cyclosporine A liposomal complex.

9. The method of claim 8, wherein said dose of dilauroylphosphatidylcholine-cyclosporine A liposomal complex comprises a concentration of cyclosporine A of about 5.0 mg cyclosporine A/ml solution in the nebulizer at a cyclosporine A: dilauroylphosphatidylcholine weight ratio of about 1:7.5.

10. The method of claim 1, wherein said dose of a lipid-anticancer drug liposomal complex is a dose of a dilauroyl phosphatidylcholine-paclitaxel liposomal complex.

11. The method of claim 10, wherein said dose of said dilauroylphosphatidylcholine-paclitaxel liposomal complex comprises a concentration of paclitaxel of about 10.0 mg paclitaxel/ml solution in the nebulizer at a paclitaxel: dilauroylphosphatidylcholine weight ratio of about 1:10.

12. The method of claim 1, further comprising the step of:
concurrently administering a continuing dose of said lipid-drug enhancer liposomal complex with said lipid-anticancer drug complex via aerosolization from a nebulizer, wherein said lipid-drug enhancer liposomal complex is mixed with said lipid-anticancer drug complex in the nebulizer.

13. The method of claim 12, wherein said dose of lipid-drug enhancer complex is a dose of a dilauroylphosphatidylcholine-cyclosporine A liposomal complex.

14. The method of claim 13, wherein said dose of dilauroylphosphatidylcholine-cyclosporine A liposomal complex comprises a concentration of cyclosporine A of about 5.0 mg paclitaxel/ml solution at a cyclosporine A: dilauroylphosphatidylcholine weight ratio of about 1:7.5 prior to mixing in the nebulizer.

15. The method of claim 12, wherein said dose of lipid-anticancer drug complex is a dose of a dilauroylphosphatidylcholine-paclitaxel liposomal complex.

16. The method of claim 15, wherein said dose of dilauroylphosphatidylcholine-paclitaxel liposomal complex comprises a concentration of paclitaxel of about 10.0 mg paclitaxel/ml solution at a paclitaxel: dilauroylphosphatidylcholine weight ratio of about 1:10 prior to mixing in the nebulizer.

17. A method of inhibiting growth of lung metastases in an individual comprising the steps of:
administering a dose of a dilauroylphosphatidylcholine-cyclosporine A liposomal complex; and, in sequence,
administering a dose of a dilauroylphosphatidylcholine-paclitaxel liposomal complex, both of said liposomal complexes delivered via aerosolization from a nebulizer; whereby said cyclosporine A and said paclitaxel inhibit growth of lung metastases in the individual.

18. The method of claim 17, wherein the sequential administration of said liposomal complexes is repeated at least once.

19. The method of claim 17, wherein said dose of dilauroylphosphatidylcholine-cyclosporine A liposomal complex comprises a concentration of cyclosporine A of about 5.0 mg cyclosporine A/ml solution in the nebulizer at a cyclosporine A:dilauroylphosphatidylcholine weight ratio of about 1:7.5.

20. The method of claim 17, wherein said dose of dilauroylphosphatidylcholine-paclitaxel liposomal complex comprises a concentration of paclitaxel of about 10.0 mg paclitaxel/ml solution in the nebulizer at a paclitaxel: dilauroylphosphatidylcholine weight ratio of about 1:10.

21. The method of claim 17, wherein said aerosol comprises about 5% to about 10% carbon dioxide.

22. A method of inhibiting growth of lung metastases in an individual comprising the steps of:
administering a dose of a dilauroylphosphatidylcholine-cyclosporine A liposomal complex via aerosolization from a nebulizer; and, in sequence,
administering a dose of a dilauroylphosphatidylcholine-paclitaxel liposomal complex while concurrently administering a continuing dose of said dilauroylphosphatidylcholine-cyclosporine A liposomal complex via aerosolization from a nebulizer wherein said dilauroylphosphatidylcholine-cyclosporine A liposomal complex is mixed with said dilauroylphosphatidylcholine-paclitaxel liposomal complex in the nebulizer,
whereby said cyclosporine A and said paclitaxel inhibit growth of lung metastases in the individual.

23. The method of claim 22, wherein the sequential and concurrent administration of said liposomal complexes is repeated at least once.

24. The method of claim 22, wherein said dose of dilauroylphosphatidylcholine-cyclosporine A liposomal complex comprises a concentration of cyclosporine A of about 5.0 mg cyclosporine A/ml solution at a cyclosporine A:dilauroylphosphatidylcholine weight ratio of about 1:7.5 in the nebulizer for both the first administration of the dilauroylphosphatidylcholine-cyclosporine A liposomal complex and prior to mixing in the nebulizer for the continuing administration with said dilauroylphosphatidylcholine-paclitaxel liposomal complex.

25. The method of claim 22, wherein said dose of dilauroylphosphatidylcholine-paclitaxel liposomal complex comprises a concentration of paclitaxel of about 10.0 mg paclitaxel/ml solution at a paclitaxel: dilauroylphosphatidylcholine weight ratio of about 1:10 prior to mixing in the nebulizer for the continuing administration with said dilauroylphosphatidylcholine-cyclosporine A liposomal complex.

26. The method of claim 22, wherein said aerosol comprises about 5% to about 10% carbon dioxide.

* * * * *